(12) United States Patent
Coperet

(10) Patent No.: US 7,289,938 B2
(45) Date of Patent: Oct. 30, 2007

(54) METHOD AND A DEVICE FOR DETECTING DISCONTINUITIES IN A MEDIUM

(75) Inventor: Philippe Coperet, Meaux (FR)

(73) Assignee: Socomate International, La Chapelle (FR)

( * ) Notice: Subject to any disclaimer, the term of this patent is extended or adjusted under 35 U.S.C. 154(b) by 0 days.

(21) Appl. No.: 10/546,125

(22) PCT Filed: Feb. 24, 2004

(86) PCT No.: PCT/EP2004/002568

§ 371 (c)(1), (2), (4) Date: Apr. 4, 2006

(87) PCT Pub. No.: WO2004/074864

PCT Pub. Date: Sep. 2, 2004

(65) Prior Publication Data

US 2006/0206275 A1   Sep. 14, 2006

(30) Foreign Application Priority Data

Feb. 24, 2003  (FR) .................................. 03 02255

(51) Int. Cl.
*G06K 9/00* (2006.01)
(52) U.S. Cl. .................... 702/189; 702/10; 702/14; 382/115; 600/443
(58) Field of Classification Search ................ 702/101, 702/141, 189, 10, 14; 73/597, 598, 600, 73/602, 623, 627, 629; 367/14, 21, 37, 38, 367/48, 49, 73; 600/407, 442, 443, 446; 382/115
See application file for complete search history.

(56) References Cited

U.S. PATENT DOCUMENTS

| | | | |
|---|---|---|---|
| 4,413,521 A * | 11/1983 | Van Kemenade | 73/626 |
| 4,441,369 A | 4/1984 | Lessard et al. | |
| 4,609,994 A * | 9/1986 | Bassim et al. | 702/39 |
| 5,319,554 A | 6/1994 | Padhi | |
| 5,428,999 A | 7/1995 | Fink | |
| 5,706,194 A * | 1/1998 | Neff et al. | 702/14 |
| 5,921,932 A * | 7/1999 | Wright et al. | 600/447 |
| 5,928,152 A * | 7/1999 | Wright et al. | 600/447 |
| 6,016,285 A * | 1/2000 | Wright et al. | 367/11 |
| 6,018,498 A * | 1/2000 | Neff et al. | 367/72 |
| 6,049,508 A | 4/2000 | Deflandre | |
| 6,049,509 A | 4/2000 | Sonneland et al. | |
| 6,212,421 B1 * | 4/2001 | Vo-Dinh et al. | 600/407 |
| 6,928,181 B2 * | 8/2005 | Brooks | 382/115 |
| 2006/0120217 A1 * | 6/2006 | Wu et al. | 367/32 |

FOREIGN PATENT DOCUMENTS

| | | |
|---|---|---|
| GB | 1175700 | 12/1969 |
| WO | WO 02-03099 A2 | 1/2002 |

* cited by examiner

*Primary Examiner*—Carol S. W. Tsai
(74) *Attorney, Agent, or Firm*—Frost Brown Todd, LLC

(57) ABSTRACT

A method and a device for detecting discontinuities in a medium by detecting maxima, e.g. in an echo signal of an ultrasound excitation of the media, with maxima corresponding to a given discontinuity being grouped together as a function of coherence criteria applied to the maxima.

12 Claims, 4 Drawing Sheets

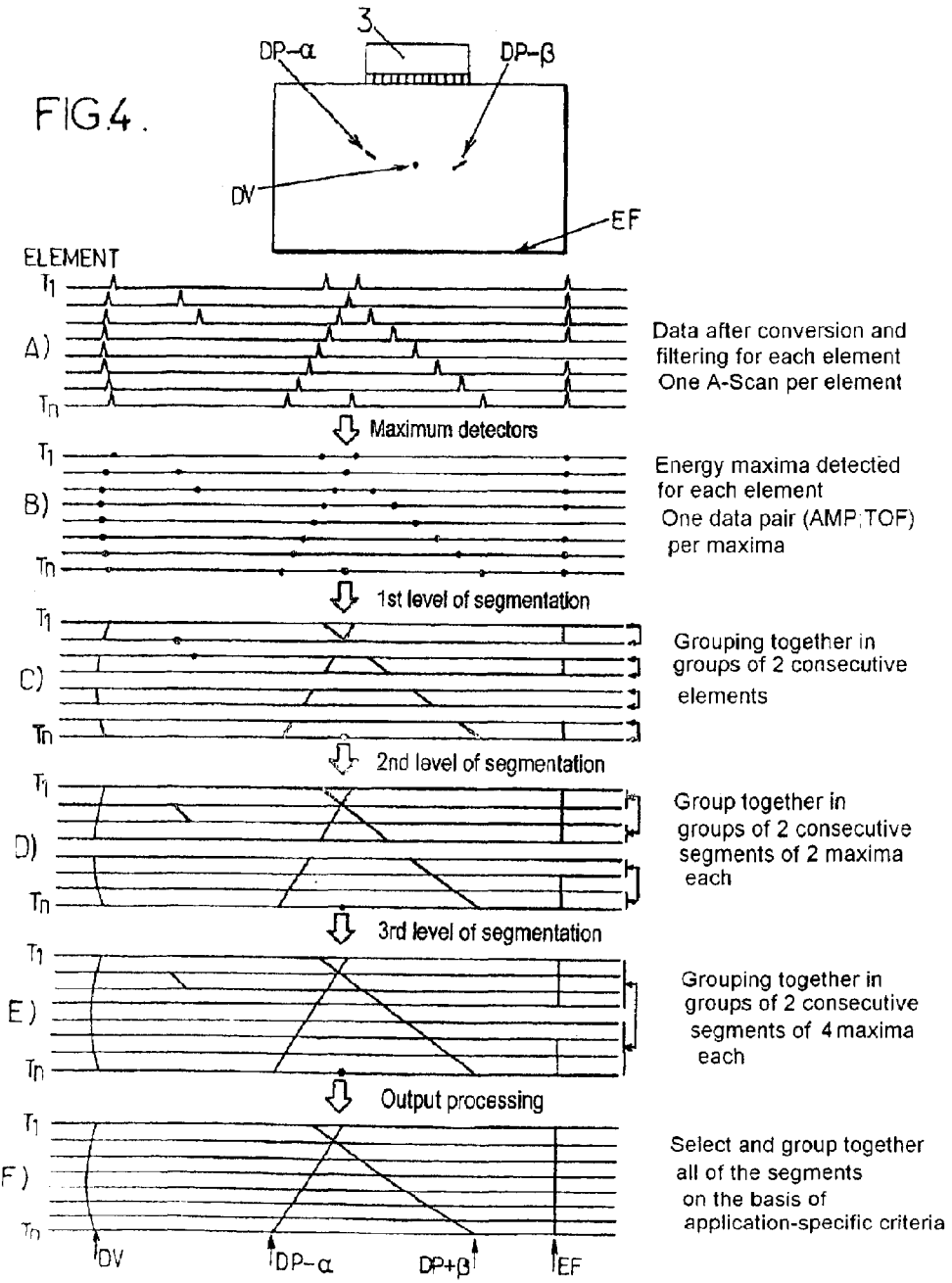

METHOD AND A DEVICE FOR DETECTING DISCONTINUITIES IN A MEDIUM

The present invention relates to methods and devices for detecting discontinuities in a medium.

More particularly, the invention relates to a method and to a device implementing the operations consisting in:

- generating an emission wave in the medium, such as an ultrasound acoustic wave, by means of at least one emitter element;
- picking up, by means of a matrix of receiver elements $T_j$, a response wave transmitted through the medium in response to the emission wave, and transforming it into an analog response signal;
- digitizing the response signal produced by each receiver element $T_j$; and
- in the response signal produced by each receiver element $T_j$ and as digitized, selecting maxima corresponding to values of the response signal that are greater than a threshold value.

Document FR-A-2 696 573 describes an example of a method implementing the above-specified operations. In that method, each emitter element and each receiver element is constituted by the same transducer in a matrix of transducers all belonging to the same probe. The emission signal is an acoustic signal and it is reflected by a reflector such as a discontinuity in the medium. The reflected signal is then time-reversed and re-emitted in order to focus the energy of the signal on the reflector, thereby automatically compensating for irregularities in the propagation of ultrasound in media that are not uniform and also compensating for errors in probe/medium positioning. In that method, the acoustic signal is said to be focused by "time-reversal".

That prior art method is not of interest when it is desired to detect a discontinuity in a medium that is moving relative to the assembly comprising the emitter and the receivers. In practice, the zone of the medium in which re-emission takes place must coincide as closely as possible with the zone in which the signal was originally emitted. In order to obtain good results, and in particular good depth resolution, it is necessary to perform a plurality of time reversals in the same zone, and that is not compatible with the time available for inspection in order to detect a discontinuity in a medium that is moving relative to the assembly comprising the emitter and the receivers, at least once such movement becomes relatively fast.

A particular object of the present invention is to provide a method and a device which make it possible to obtain good detection of a discontinuity in a medium, regardless of the shape, the position, and the orientation of said discontinuity, and without having recourse to the method of focusing by time-reversal, so as to be able to use the invention even when the probe is moving quite quickly relative to the medium.

To this end, the invention provides a method of detecting discontinuities in a medium, which method, in addition to the characteristics mentioned above, is characterized by the fact that it comprises an operation of processing the maxima, which operation consists in applying at least one coherence criterion to the maxima selected from the set of digitized response signals so as to group together maxima corresponding to the same discontinuity.

By means of these dispositions, the processing of the signal produced by the detector elements is performed in self-adaptive manner. Resolution in space and in time is obtained by seeking coherence in the signal that is produced and does not require focusing by time-reversal. In the invention, the signal is produced and processed in real time, with the same performance being conserved even when the relative movement of the probe relative to the medium is fast or very fast (e.g. at a speed substantially equal to or greater than 30 meters per second (m/s), as is the case when inspecting rails for railway lines).

In preferred implementations of the method of the invention, recourse may optionally be had in addition to one or more of the following dispositions:

the operation consisting in selecting the maxima comprises:
- sliding detection of peaks above a dynamic noise level, said detection being performed by assessing the slope of each response signal produced by a receiver element $T_j$; and
- identifying the maximum of each peak;

the operation of processing the maxima includes a first coherence test consisting in grouping together in a segment l two maxima detected on two consecutive receiver elements j and j+1 if $$|TOF(j)_{i=1 \text{ to } k} - TOF(j+1)_{i'=1 \text{ to } k'}| \leq T$$

in which:
- $TOF(j)_{i=1 \text{ to } k}$ is the time position of the maximum i, where i=1 to k, within the response signal produced by the element j;
- $TOF(j+1)_{i'=1 \text{ to } k'}$ is the time position of the maximum i' with i'=1 to k' in the response signal produced by the element j+1; and
- $T = t + \epsilon$ with $$t = \frac{\sin\alpha}{v} p,$$

$\alpha$ being the desired maximum deflection angle, p being the distance between the receivers j and j+1, v being the wave speed in the medium, and $\epsilon$ being the tolerance of the processing operation to calculation errors and to mechanical dispersion;

the operation of processing the maxima further includes a second coherence test consisting in retaining a segment l only if $$|AMP(j)_l - AMP(j+1)_l| \leq \Delta A$$

in which:
- $AMP(j)_l$ and $AMP(j+1)_l$ are the amplitudes respectively of the maxima detected on two consecutive receiver elements j and j+1 in a segment l; and
- $\Delta A$ is a predetermined value for the difference accepted for the amplitudes of maxima grouped together in a single segment;

the operation of processing maxima further includes a third coherence test consisting in grouping together as a single segment two segments l and l+1 of two pairs of consecutive receiver elements j, j+1, j+2, and j+3 if $$|(TOF(j+1))_l - (TOP(j+2))_{l+1}| \leq T$$

and $$|\text{slope } S(l) - \text{slope } S(l+1)| \leq \Delta P$$

in which:
- $(TOF(j+1))_l$ and $(TOP(j+2))_{l+1}$ are the time positions of two consecutive maxima belonging to two consecutive segments l and l+1; and slope S(l) and slope S(l+1) are the respective slopes of the segments l and l+1 and ΔP is a predetermined value for the difference accepted for the slopes of two consecutive segments;

the operation of processing maxima further comprises a fourth coherence test consisting in grouping together two segments l and l+1 only if $$|AMP(j+1)_l - AMP(j+2)_{l+1}| \leq \Delta A$$

in which:

AMP$(j+1)_l$ and AMP$(j+2)_{l+1}$ are the amplitudes respectively of two consecutive maxima belonging to two consecutive segments l and l+1; and ΔA is a predetermined value for the difference accepted for the amplitudes of grouped-together maxima; and the method includes an operation in which segments or a set of segments are selected in accordance with at least a fifth criterion so as to characterize discontinuities of the medium, the fifth criterion relating to a parameter selected from the list comprising: a minimum number of maxima grouped together in a segment; the amplitude of the sum of the maxima of a segment or a set of segments; an acceptable loss value; an angular response value; and a volume response value.

The "acceptable loss value" parameter corresponds to the number of maxima distributed over a certain number of signals produced by the detector elements $T_j$ that can be ignored. The "angular response value" parameter makes it possible to ignore segments and not group them together unless they lie in a given angular window. The "volume response value" parameter enables segments to be ignored and not grouped together unless they correspond to a three-dimensional discontinuity, i.e. a discontinuity which is identified by a segment of curved shape.

In another aspect, the invention provides a device for implementing the method of the invention. The device comprises:

at least one emitter for generating an emission wave such as an ultrasound wave in the medium by means of at least one emitter element;

a matrix of n receiver elements j, for picking up a response wave transmitted in the medium in response to the emission wave and for transforming it into an analog response signal;

a set of n analog-to-digital converters, each analog-to-digital converter being connected in series with a receiver element $T_j$ to digitize the analog response signal produced by each receiver element $T_j$;

a set of n programmable logic circuits, each of these circuits being connected in series with an analog-to-digital converter to select, from the digitized response signal from each receiver element, maxima corresponding to response signal values greater than a dynamic threshold value; and a set of digital signal processors for testing the maxima detected in the set of digitized response signals with at least one coherence criterion so as to group together maxima corresponding to the same discontinuity.

In preferred embodiments of the device of the invention, recourse may optionally be had in addition to one or more of the following dispositions:

a first group of processors in the set of digital processors are arranged in a tree structure to group together successive maxima into segments corresponding to the same discontinuity in the medium; and a second group of processors in the set of digital processors are arranged in parallel, each processor in the second group performing specific processing for characterizing discontinuities in the medium on the basis of the maxima that have been grouped together by the first group of processors.

Other aspects, objects, and advantages of the device of the invention appear on reading the following description of an embodiment thereof.

The invention will also be better understood with the help of the drawings, in which:

FIGS. 4A to 4F are diagrams showing the processing of signals such as those shown in FIG. 3b during various steps of the method implemented by the device shown in FIG. 2.

In the various figures, the same references designate elements that are identical or similar.

An embodiment of the device of the invention, and an example of the method implemented by said device are described below in illustrative and non-limiting manner.

Figure 1A:
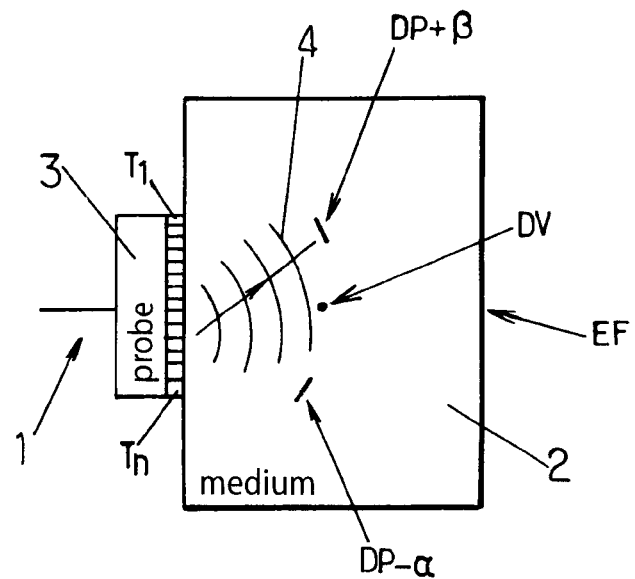
FIGS. 1a and 1b are diagrams showing a medium being subjected to sound using a device in accordance with the invention.
Figure 1B:
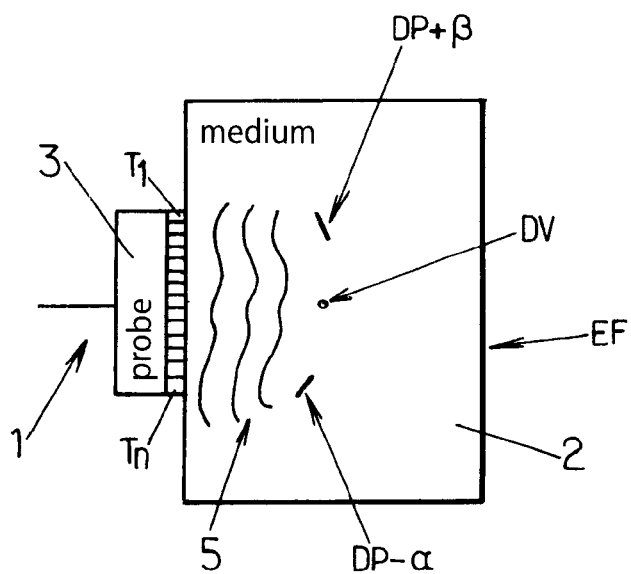

In this example, shown in FIGS. 1a and 1b, the device of the invention is a device 1 for using ultrasound to detect discontinuities in a medium. More precisely, the device 1 is for detecting such discontinuities in a medium, in this case a part 2, traveling at very high speed relative to the device 1.

The device and the method of the invention as described below are applicable in particular to non-destructive inspection of manufactured parts such as metal tubes, non-destructive inspection of railway rails, etc., with automatic systems and/or portable appliances.

The device 1 includes a probe 3 constituted by transducer elements $T_j$ with j=1 to n.

These transducer elements $T_j$ constitute both emitter elements and receiver elements. Thus, as shown in FIG. 1a, an emission wave 4 is emitted into the part 2 in the form of a pulse.

As shown in FIG. 1b, the medium of the part 2 responds to this emission wave 4 by reflecting a response wave 5, also referred to as an "echo". The term "shot" is used to designate the period covering both the emission of a pulse and the following acquisition period, i.e. the period corresponding to the return of the response wave 5.

The response wave 5 is representative of discontinuities in the medium of the part 2. By way of example, FIGS. 1a and 1b show a discontinuity presenting negative plane angular reflection DP−α, a discontinuity presenting positive plane angular reflection DP+β, a discontinuity with volume reflection DV, and a discontinuity with reflection around zero degrees, such as the background echo EF.

The type of transducer may be selected as a function of the application for which implementation of the method of the invention is intended and/or in order to obtain the best value for money in terms of quality/price ratio, since it does not have any direct influence on the method of the invention. By way of example, the transducers may be piezoelectric transducers. This type of transducer and the way in which they are used are well known to the person skilled in the art.

The elements $T_j$ of the probe 3 form an array which may be distributed in linear form, in matrix form, or randomly.

Figure 2:
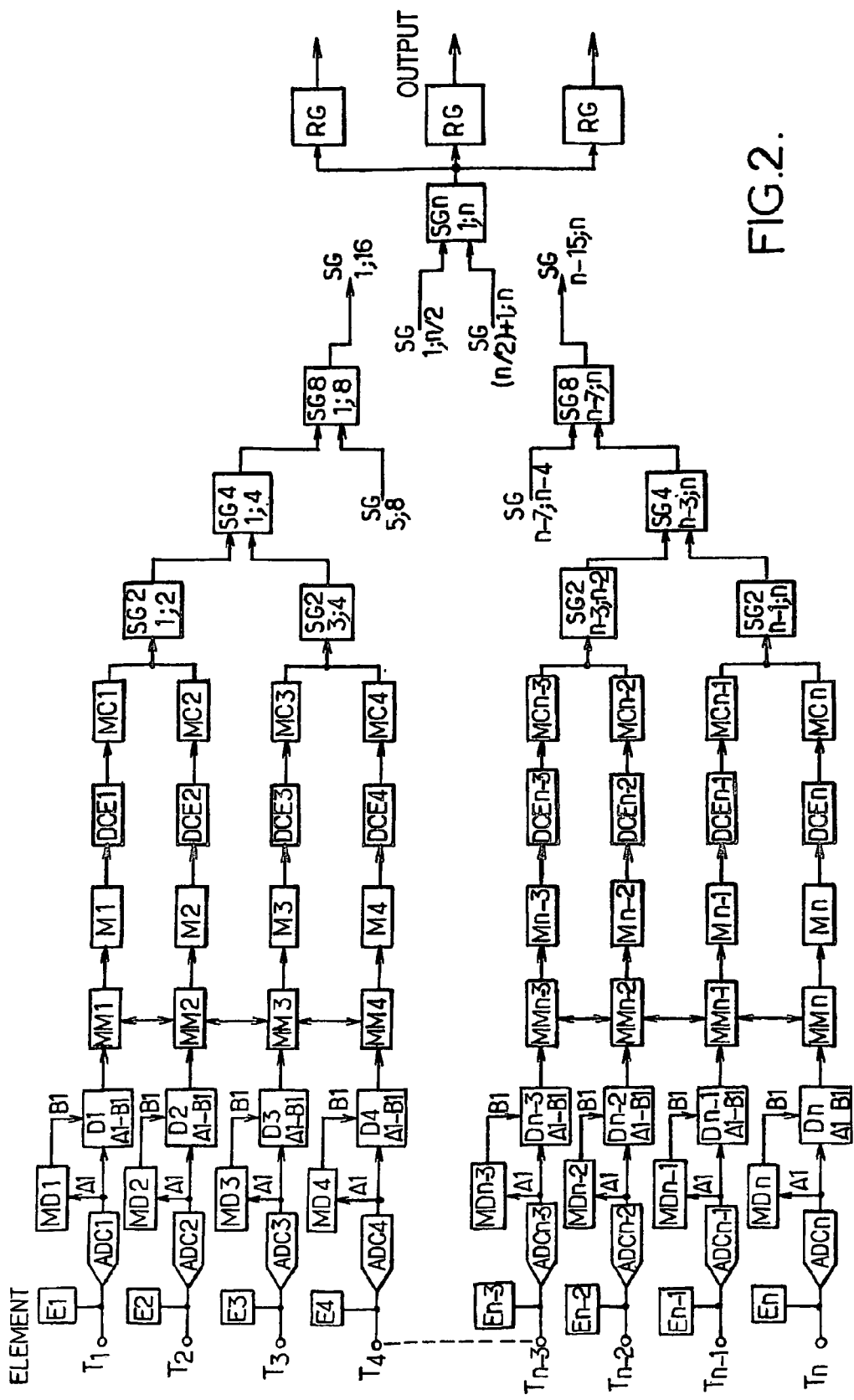
FIG. 2 is a diagram summarizing the architecture of an example of a device of the invention.

As shown in FIG. 2, generators E1 to En generate signals for exciting the elements $T_j$ so as to subject the part 2 for inspection correctly to sound. The generators E1 to En may be of mono-polar or bipolar logic type or they may be of linear type. The type of emitter may be selected as a function of the application for which implementation of the method of the invention is intended and/or in order to obtain best value for money since it has no direct influence on the method of the invention.

The generators E1 to En are driven in such a manner as to form a focused or non-focused multidirectional beam, for example, as described in French patent application No. FR 01/12516.

In variants of the method described herein, the generators E1 to En can be driven so as to form a signal in a single direction that is focused or not focused, or indeed that is cylindrical or spherical, by emitting from a single element $T_j$ of a probe that is respectively linear or in matrix form.

On reception, the waves 5 picked up by the elements $T_j$ of the probe 3 are transformed by the elements $T_j$ into analog signals which are applied directly to analog-to-digital converters CAN1 to CANn in which they are sampled and digitized.

In order to avoid any correction of analog gain upstream and in order to guarantee linearity of the digitized signals, the analog signals having a working dynamic range of about 80 decibels (dB), so it is necessary to use converters CAN1 to CANn operating on a minimum of 14 bits.

In order to obtain satisfactory time accuracy, of the order of $\lambda/10$ (where $\lambda$ is the wavelength of the response wave), it is possible to use two digitizing techniques described below as examples, depending on the operating frequency of the probe 3 used.

In one of these techniques, direct sampling is performed at about ten times the probe frequency. For example, sampling is performed at 50 megahertz (MHz) for a probe operating at 3 MHz with a passband of 65%.

In the other one of these techniques, sampling is performed at about three times the probe frequency, and resolution is increased by interpolating by digital filtering. For example, sampling is performed at 50 MHz and interpolation is performed with a factor 4 for a probe operating at 15 MHz and a passband of 80%.

The device of the invention thus enables probes 3 to be used at frequencies lying in the range 1 MHz to 20 MHz, thereby covering most applications.

In the implementation of the method of the invention described herein, the second technique has been selected with sampling at a frequency of about 64 MHz and with a digital interpolator operating with a factor of 3, for a probe having a nominal frequency of 15 MHz and a passband of 80%.

The digitized signals are then applied to maximum detectors DCE1 to DCEn.

In order to detect maxima properly in the digitized signals, the signals must present a sufficient signal/noise ratio which is usually the case in the great majority of industrial inspection applications such as inspecting rails, tubes, metal sheets, or composites.

Nevertheless, if the signal/noise ratio is not necessarily sufficient, for example in large-grained materials, it is possible to improve the signal/noise ratio by inserting two types of processing between the analog-to-digital converters CAN1 to CANn and the maximum detectors DCE1 to DCEn, depending on whether the noise is steady or random.

For steady noise of the "shape echo" type associated with the shape of the part which is being inspected for discontinuities, the noise can be stored by being acquired in a zone that does not have defects, and can then be subtracted from acquisitions during inspection prior to detecting maxima. This noise can be subtracted in full or in part, e.g. for the purpose of conserving an input echo and a background echo.

When in the presence of random electronic noise and/or random acoustic noise, an average of consecutive shots and/or over recurrent paths and/or over elements close to one another can enable the signal/noise ratio to be improved. For example, an average over ten consecutive shots, over two recurrent paths, and over five close elements, giving in all an average of 100 acquisitions can theoretically improve the signal/noise ratio by 20 dB.

Both of those two processes can be performed simultaneously when both types of noise coexist.

Thus, optionally, storage circuits MD1 to MDn and calculator circuits D1 to Dn are interposed after the outputs from the converters CAN1 to CANn. They enable steady noise of the "shape echo" type to be reduced when such noise disturbs the operation of the maximum detectors located downstream therefrom. To do this, shape echoes are stored in the storage circuits MD1 to MDn during a stage of calibrating the device of the invention. The stored data is subsequently subtracted from current data by the calculator circuits D1 to Dn during the stage of detecting discontinuities proper.

This type of operation is possible because of the large dynamic range of the converters and whenever detection conditions are very stable.

Similarly, and likewise in optional manner, other storage circuits MM1 to MMn and averaging circuits M1 to Mn can be interposed at the outputs from the converters CAN1 to CANn or of the calculator circuits D1 to Dn. These serve to improve the ratio of signal to random noise when it is not sufficient to enable the maximum detectors DCE1 to DCEn situated downstream to operate property. For this purpose, the data is stored in the storage circuits MM1 to MMn and is averaged, as mentioned above over shots and/or over recurrent paths, and/or over close elements, by the circuits for averaging M1 to Mn.

The maximum detectors DCE1 to DCEn receive the raw signals from the analog-to-digital converters or the signals as filtered by one or the other of both of the above-described processes.

They thus receive signals clocked at 64 MHz during an acquisition period that may last for several hundreds of microseconds in common applications, giving several tens of thousands of samples per detector element $T_j$ (with j=1 to n) of the probe 3.

The maximum detectors DCE1 to DCEn seek the maxima or peaks that stand clear of noise, and they store the amplitudes AMP and the positions TOF thereof in storage circuits MC1 to MCn. This operation is illustrated in FIGS. 3a, 3b, and 4A, 4B.

Detection proper of maxima is performed as follows for each of the detector elements $T_j$ of the probe 3, and without any correlation between adjacent elements.

Figure 3A:
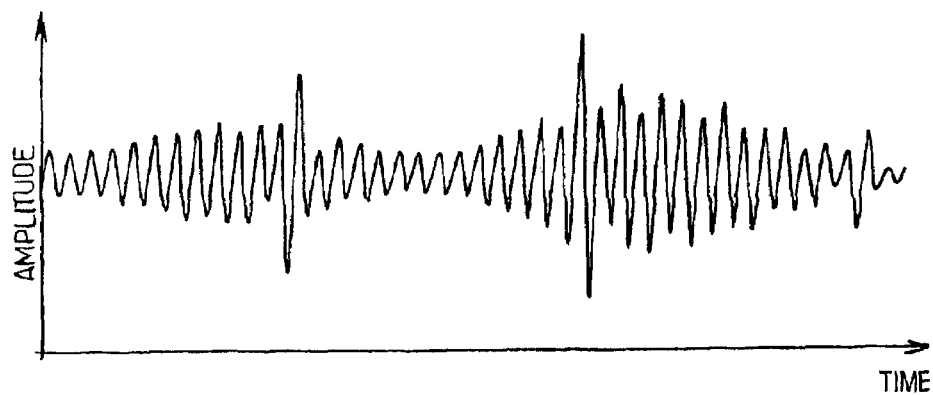
FIGS. 3a and 3b are diagrams showing an example of a digitized signal taken from a detector element of the device of the invention, respectively before and after smoothing.

The signals received by the maximum detectors DCE1 to DCEn are of the type shown in FIG. 3a. In the detectors DCE1 to DCEn, they are subjected to rectification and lowpass type filtering so as to extract therefrom an energy curve of the kind shown in FIG. 3b.

Sliding maximum detection is then performed over m samples (e.g. m=10) along this energy curve so as to determine the dynamic noise level above which maxima can be sought.

Figure 3B:
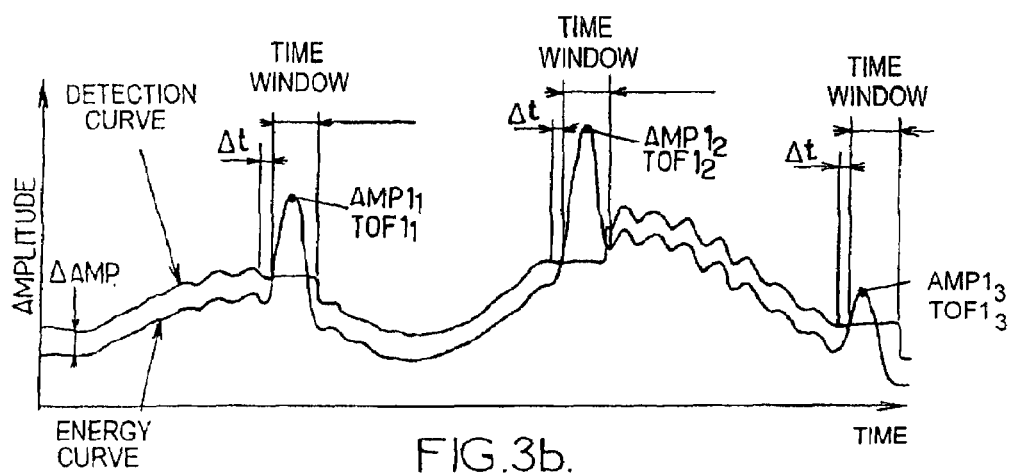

A test is then performed to determine whether the sample situated at Δt of the sliding detector is greater than the dynamic noise level determined at the preceding step, plus a value Δamp (see the detection curve of FIG. 3b). This step makes it possible to detect variation in the energy curve that corresponds to the slope and thus to the rise time of the signal produced by each detector element $T_j$, e.g. Δt+4 samples and Δamp=+3 conversion levels of the converters CAN1 to CANn.

If the above test is positive (see FIG. 3b),
the dynamic noise sliding detector is blocked;
a "time window" is opened with width equal to approximately the width of an echo, given the spectrum of the emission wave and the passband of the probe 3;
the greatest value of the signal contained in the "time window" is sought and its amplitude AMP and position TOF are stored (FIGS. 4A, 4B); and
the "time window" is closed and the dynamic noise sliding detector is unblocked, so the echo is not taken into account.

About ten maxima per detector element $T_j$ (for j=1 to n) of the probe 3 suffice to characterize the acoustic image in most applications, thus representing data compression by a factor of about 1000.

The maximum detectors DCE1 to DCEn are, for example, small capacity programmable logic circuits. They are therefore of very reasonable cost.

Segmentation circuits SG2 to SGn thereafter seek coherence between the maxima stored in the memories MC1 to MCn in pyramid manner, in groups of two:
the segmentation circuits SG2 select and group together in segments of two maxima each, the maxima detected in the digitized signals coming from two consecutive detector elements $T_j$ of the probe 3;
the segmentation circuits SG4 select and group together in segments of four maxima each, the maxima detected in the digitized signals from two consecutive segments selected by the preceding segmentation circuits for two consecutive detector elements $T_j$ of the probe 3;
the segmentation circuits SG8 select and group together in segments of eight maxima each, the maxima detected in the digitized signals coming from two consecutive segments as selected by the preceding segmentation circuits for four consecutive detector elements $T_j$ of the probe 3, and so on;
and finally, the circuit SGn selects and groups together the maxima detected in the digitized signals coming from two consecutive segments selected by the preceding segmentation circuits for n/2 consecutive detector elements $T_j$ of the probe 3.

This structure presents the advantage that each segmentation circuit SG2 to SGn has available the duration of one shot for performing the corresponding algorithm, regardless of the number of elements $T_j$ in the probe 3. The segmentation circuits SGr of rank r process the signal corresponding to one shot while the segmentation circuits SGr+1 of the next rank r+1 process the signal corresponding to the preceding shot, and so on.

The device of the invention thus operates in real time regardless of the number of elements $T_j$ of the probe 3, with a synchronous delay of "pipe-line" type equal to the binary exponent of the number of elements $T_j$ in the probe 3.

For each segmentation circuit SG4 to SGn, if the maxima have not been grouped together during preceding segmentation operations:
one of the maxima is grouped with a segment in a new segment if it satisfies the criteria for grouping together two segments as described above; the missing slope may be calculated over the imaginary segment created with this maximum and the last maximum of the real segment; and
two of these maxima are grouped together in a single segment if they satisfy the first criterion and possibly also the second criterion, in groups of two signals produced by consecutive detector elements $T_j$, as described above.

If a maximum does not correspond to the above cases, it is conserved unchanged and transferred to the following segmentation circuits, for possible processing thereby. The maxima that are not treated by the set of segmentation circuits are treated by the grouping circuit RG.

The segmentation circuits SG2 to SGn are digital signal processors (DSPs). They are suitable for performing the above-described segmentation algorithms in real time. They also have communications lines enabling data to be transferred between two segmentation circuits SGr and SG2r.

A grouping circuit RG recovers the data from the last segmentation circuit SGn and processes it as a function of criteria associated with the application, either directly in order to characterize a discontinuity, or else to reconstruct a conventional A-SCAN, which is then used in conventional manner by "time windows".

The grouping circuit RG is likewise constituted by a DSP and it has available to it the duration of one shot for performing the corresponding processing.

In complex applications, it is possible to put a plurality of DSPs in parallel at this level of the processing, in which case each of them can perform some specific task, as in the example of FIG. 4:
processing volume responses;
processing positive plane angular responses;
processing negative plane angular responses; and
processing responses around zero degrees including the background echo.

We return to the search for coherence by the segmentation circuits SG2 to SGn (see FIGS. 4B to 4F).

As shown in FIGS. 4B and 4C, the segmentation circuits SG2 seek for coherence by performing a first and optionally a second coherence test.

The first coherence test consists in grouping together in a segment l two maxima detected on two consecutive receiver elements j and j+1 if $$|TOF(j)_{i=1\ to\ k} - TOF(j+1)_{i'=1\ to\ k'}| \leq T$$

in which:
$TOF(j)_{i=1}$ to k is the time position of the maximum i, where i=1 to k, within the response signal produced by the element j;
$TOF(j+1)_{i'=1\ to\ k'}$ is the time position of the maximum i' with i'=1 to k' in the response signal produced by the element j+1; and
T=t+6 with $$t = \frac{\sin\alpha}{v} p,$$

α being the desired maximum deflection angle, p being the distance between the receivers j and j+1, v being the wave speed in the medium, and $\epsilon$ being the tolerance of the processing operation to calculation errors and to mechanical dispersion (associated with the probe 3 being guided relative to the part 2 and with the orientation of the discontinuity).

For example, if the maximum deflection angle $\alpha$ is equal to 90°, if the pitch of the probe is equal to 0.5 mm, and if the propagation speed of ultrasound in the medium is equal to 3.230 m/s, then t is equal to 155 nanoseconds (ns). Thus, if $\epsilon$ is equal to 10% t, then T equals 170 ns.

The second coherence test consists in conserving a segment l only if:

$$|AMP(j)_l - AMP(j+1)_l| \leq \Delta A$$

in which:
AMP(j)$_l$ and AMP(j+1)$_l$ are the amplitudes respectively of the maxima detected on two consecutive receiver elements j and j+1 in a segment l; and $\Delta A$ is a predetermined value for the difference accepted for the amplitudes of maxima grouped together in a single segment.

As shown in FIGS. 4D and 4E, the segmentation circuits SG4 to SGn seek coherence by performing a third and optionally a fourth coherence test.

The third coherence test consists in grouping together in a single segment two segments l and l+1 of two pairs of consecutive receiver elements j, j+1, j+2, and j+3 if $$|(TOF(j+1))_l - (TOP(j+2))_{l+1}| \leq T$$

and $$|\text{slope } S(l) - \text{slope } S(l+1)| \leq \Delta P$$

in which:
(TOF(j+1))$_l$ and (TOP(j+2))$_{l+1}$ are the time positions of two consecutive maxima belonging to two consecutive segments l and l+1; and slope S(l) and slope S(l+1) are the respective slopes of the segments l and l+1 and $\Delta P$ is a predetermined value for the difference accepted for the slopes of two consecutive segments.

The fourth coherence test consists in grouping together two segments l and l+1 only if $$|AMP(j+1)_l - AMP(j+2)_{l+1}| \leq \Delta A$$

in which:
AMP(j+1)$_l$ and AMP(j+2)$_{l+1}$ are the amplitudes respectively of two consecutive maxima belonging to two consecutive segments l and l+1; and $\Delta A$ is a predetermined value for the difference accepted for the amplitudes of grouped-together maxima.

As shown in FIG. 4F, the grouping circuit RG selects the segments or a set of segments in accordance with at least one fifth criterion so as to characterize discontinuities in the medium, this fifth criterion relating to a parameter selected from the list comprising a minimum number of maxima grouped together in a segment, the amplitude of the sum of the maxima in a segment or a set of segments, an acceptable loss value, an angular response value, and a volume response value. Thus, in FIG. 4F, the reconstruction of the segment corresponding to the background echo EF makes use of an acceptable loss value, reconstruction of the segment corresponding to a volume defect DV makes use of a volume response value; and reconstructing segments corresponding to plane defects DP-$\alpha$ and DP+$\beta$ makes use of an angular response value. It should be observed that taking account of a minimum number of maxima makes it possible to eliminate a segment constituted by two maxima in FIGS. 4D and 4E.

It is thus possible to see that the device of the invention enables defects to be detected regardless of their orientation and their shape, regardless of whether they are plane defects or volume defects, and that there is a very good signal/noise ratio because detections that do not satisfy the output selection criteria are rejected.

It can thus be seen that the device of the invention enables defects to be characterized very well by detecting the real angle if the defect is a plane defect, or a curved response, if the defect is a volume defect.

In addition, the method of the invention makes it possible to avoid using mechanisms as bulky and as expensive as those required for positioning and moving single element detectors as implemented in certain prior art methods. The method of the invention also makes it much easier to adjust such machines because of the flexibility with which the emission signal can be controlled electronically. Thus, the method of the invention is very tolerant concerning mechanical guidance of the part 2 for inspection relative to the probe 3.

The method of the invention is also very tolerant to variations in ultrasound propagation speed, whether general or local.

The device of the invention enables inspection to be performed quickly, defects being detectable in all directions simultaneously with an inspection pitch equal to the width of the probe 3.

The detection method and its processing algorithms are simultaneously well adapted and very simple.

The value for money of the device of the invention is excellent.

Since the method is one of processing an acoustic image and not one of reconstructing an ultrasound beam, the definition criteria of the probe are very different. In particular, it is possible to reduce considerably the number of detector elements $T_j$ in certain applications, thereby leading to a further reduction in cost.

The method of the invention applies to all types of probe whether linear or circular, and in particular to probes in a matrix configuration, given the reduction that is possible in the number of elements, a criterion that becomes essential with a matrix probe.

The invention is applicable, although not exclusively, to all kinds of inspection using ultrasound, in particular in the field of non-destructive inspection to portable appliances and to automatic systems, and in the medical field to locating appliances.

The invention is also applicable to all systems using a sensor made up of a plurality of independent elements, regardless of the physical phenomenon involved, such as eddy currents, infrasound, electromagnetic waves, etc.

The method of the invention applies in general to all multi-element sensors, whether in linear or in matrix form.

The invention claimed is:

1. A method of detecting discontinuities in a medium, the method comprising the operations consisting in:
generating an emission wave in the medium by means of at least one emitter element;
picking up, by means of a matrix of receiver elements $T_j$, a response wave transmitted through the medium in response to the emission wave, and transforming it into an analog response signal;
digitizing the response signal produced by each receiver element $T_j$; and in the response signal produced by each receiver element $T_j$ and as digitized, selecting maxima corresponding to values of the response signal that are greater than a threshold value;

wherein the method further comprises an operation of processing the maxima, which operation consists in applying at least one coherence criterion to the maxima selected from the set of digitized response signals so as to group together maxima corresponding to the same discontinuity.

2. The method according to claim 1, wherein the operation consisting in selecting the maxima comprises:

sliding detection of peaks above a dynamic noise level, said detection being performed by assessing the slope of each response signal produced by a receiver element $T_j$; and identifying the maximum of each peak.

3. The method according to claim 1, wherein the operation of processing the maxima includes a first coherence test consisting in grouping together in a segment l two maxima detected on two consecutive receiver elements j and j+1 if $$|TOF(j)_{i=1 \ to \ k} - TOF(j+1)_{i'=1 \ to \ k'}| \leq T$$

wherein:

$TOF(j)_{i=1 \ to \ k}$ is the time position of the maximum i, where i=1 to k, within the response signal produced by the element j;

$TOF(j+1)_{i'=1 \ to \ k'}$ is the time position of the maximum i' with i'=1 to k' in the response signal produced by the element j+1; and $T = t + \in$ with $t = \dfrac{\sin\alpha}{v} p$, αbeing the desired maximum deflection angle, p being the distance between the receivers j and j+1, v being the wave speed in the medium, and $\in$ being the tolerance of the processing operation to calculation errors and to mechanical dispersion.

4. The method according to claim 3, wherein the operation of processing the maxima further includes a second coherence test consisting in retaining a segment l only if $$|AMP(j)_l - AMP(j+1)_l| \leq \Delta A$$

in which:

$AMP(j)_l$ and $AMP(j+1)_l$ are the amplitudes respectively of the maxima detected on two consecutive receiver elements j and j+1 in a segment l; and $\Delta A$ is a predetermined value for the difference accepted for the amplitudes of maxima grouped together in a single segment.

5. The method according to claim 3, wherein the operation of processing maxima further includes a third coherence test consisting in grouping together as a single segment two segments l and l+1 of two pairs of consecutive receiver elements j, j+1, j+2, and j+3 if $$|(TOF(j+1)_l - (TOP(j+2))_{l+1}| \leq T$$

and $$|slope \ S(l) - slope \ S(l+1)| \leq \Delta P$$

wherein:

$(TOF(j+1))_l$ and $(TOP(j+2))_{l+1}$ are the time positions of two consecutive maxima belonging to two consecutive segments l and l+1; and slope S(l) and slope S(l+1) are the respective slopes of the segments l and l+1 and $\Delta P$ is a predetermined value for the difference accepted for the slopes of two consecutive segments.

6. The method according to claim 5, wherein the operation of processing maxima further comprises a fourth coherence test consisting in grouping together two segments l and l+1 only if $$|AMP(j+1)_l - AMP(j+2)_{l+1}| \leq \Delta A$$

in which:

$AMP(j+1)_l$ and $AMP(j+2)_{l+1}$ are the amplitudes respectively of two consecutive maxima belonging to two consecutive segments l and l+1; and $\Delta A$ is a predetermined value for the difference accepted for the amplitudes of grouped-together maxima.

7. The method according to claim 3, wherein segments or a set of segments are selected in accordance with at least a fifth criterion so as to characterize discontinuities of the medium, the fifth criterion relating to a parameter selected from the list comprising: a minimum number of maxima grouped together in a segment; the amplitude of the sum of the maxima of a segment or a set of segments; an acceptable loss value; an angular response value; and a volume response value.

8. The method according to claim 1, wherein the emission wave is an ultrasound wave in the medium.

9. A device for detecting discontinuities in a medium, the device comprising:

at least one emitter for generating an emission wave in the medium by means of at least one emitter element;

a matrix of n receiver elements j, for picking up a response wave transmitted in the medium in response to the emission wave and for transforming it into an analog response signal;

a set of n analog-to-digital converters, each analog-to-digital converter being connected in series with a receiver element $T_j$ to digitize the analog response signal produced by each receiver element $T_j$;

a set of n programmable logic circuits, each of these circuits being connected in series with an analog-to-digital converter to select, from the digitized response signal from each receiver element, maxima corresponding to response signal values greater than a dynamic threshold value; and a set of digital signal processors for testing the maxima detected in the set of digitized response signals with at least one coherence criterion so as to group together maxima corresponding to the same discontinuity.

10. The device according to claim 9, wherein a first group of processors in the set of digital processors are arranged in a tree structure to group together successive maxima into segments corresponding to the same discontinuity in the medium.

11. The device according to claim 10, wherein a second group of processors in the set of digital processors are arranged in parallel, each processor in the second group performing specific processing for characterizing discontinuities in the medium on the basis of the maxima that have been grouped together by the first group of processors.

12. The device according to claim 9, wherein the emission wave is an ultrasound wave in the medium.

* * * * *